US008093368B2

(12) United States Patent
Sakai

(10) Patent No.: US 8,093,368 B2
(45) Date of Patent: Jan. 10, 2012

(54) DR5 GENE PROMOTER AND SIAH-1 GENE PROMOTER

(75) Inventor: Toshiyuki Sakai, Kyoto (JP)

(73) Assignee: Oncolys Biopharma Inc., Tokyo (JP)

( * ) Notice: Subject to any disclaimer, the term of this patent is extended or adjusted under 35 U.S.C. 154(b) by 243 days.

(21) Appl. No.: 12/385,863

(22) Filed: Apr. 22, 2009

(65) Prior Publication Data

US 2011/0117644 A1    May 19, 2011

Related U.S. Application Data

(62) Division of application No. 10/491,622, filed as application No. PCT/IB02/04074 on Oct. 4, 2002, now abandoned.

(30) Foreign Application Priority Data

Oct. 4, 2001 (JP) .................................. 2001-309179

(51) Int. Cl.
*C07H 21/04* (2006.01)
*C12N 15/00* (2006.01)
*C12N 5/00* (2006.01)

(52) U.S. Cl. ...................... 536/24.1; 435/320.1; 435/325

(58) Field of Classification Search .......................... None
See application file for complete search history.

(56) References Cited

U.S. PATENT DOCUMENTS

2004/0248132 A1* 12/2004 Sakai .................................. 435/6
2011/0117644 A1* 5/2011 Sakai ............................ 435/325

FOREIGN PATENT DOCUMENTS

| WO | WO 98/14568 A1 | 4/1998 |
| WO | WO 98/41629 | 9/1998 |
| WO | WO 99/02653 A1 | 1/1999 |
| WO | WO 99/47540 A1 | 9/1999 |
| WO | WO 00/66156 | 11/2000 |
| WO | WO 01/053482 A1 | 7/2001 |
| WO | WO 01/55314 A2 | 8/2001 |

OTHER PUBLICATIONS

Inken Wierstra; "Sp1: Emerging roles-Bey9ond constitutive activation of TATA-less housekeeping genes", Biochemical and Biophysical Research Communications 271 (2008) 1-13.
Stephen T. Smale; "Transcription initiation from TATA-less promoters within eukaryotic protein-coding genes", Biochimica et Biophysica Acta 1351 (1997) 73-86.
Database Embl 'Online! Mar. 22, 2001, "*Homo sapiens* DR5 gene for death receptor 5, promoter and partial cds." XP002330065.
Yoshida A T et al: "Promoter structure and transcription initiation sites of the human death receptor 5/Trail-R2 gene<1>" FEBS Letters, Elsevier Science Publishers, Amsterdam, NL, vol. 507, No. 3, Nov. 2, 2001, pp. 381-385, XP004320958.
Gen Sheng Wu et al: "Killer/DR5 is a DNA damage-inducible p53-regulated death receptor gene" Nature Genetics, New York, NY, US, vol. 17, No. 2 Oct. 1997, pp. 141-143 XP002083924.
Wu G S A et al: "Killer/DR5, a Novel DNA-Damage Inducible Death Receptor Gene, Links the P53-Tumor Suppressor to Caspase Activation and Apoptotic Death" Advances in Experimental Medicine and Biology, Spring St., NY, US, vol. 465, 2000, pp. 143-151, XP001016228.
Sowa Y et al: "Butyrate as a Model for Gene-Regulating Chemoprevention and Chemotherapy" Biofactors, Oxford University Press, Oxford, GB, vol. 12, No. 1-4, 2000, pp. 283-287, XP009050386.
Nemani et al: "Activation of the Human Homolouge of the *Drosophila sina* Gene in Apoptosis and Tumor Suppression" Proceedings of the National Academy of Science of USA, National Academy of Science, Washington, US, vol. 93, No. 17. Aug. 20, 1996, pp. 9039-9042, XP000611649.
Liu J et al: "Siah-1 Mediates a Novel Beta-Catenin Degradation Pathway Linking P53 to the Adenomatous Polyposis Coliprotein" Molecular Cell, Cell Press, Cambridge, MA, US, vol. 7, May 2001, pp. 927-936, XP002949014.
Maeda A et al: "The characterization of the human Siah-1 promoter<1>" FEBS Letters, Elsevier Science Publishers, Amsterdam, NL, vol. 512, No. 1-3, Feb. 13, 2002, pp. 223-226, XP004341382.
XP 002330065; Mar. 22, 2001. "*Homo sapiens* DR5 gene for death receptor 5, promoter and partial cds."
Wu et al.: "Killer/DR5 a DNA damage-inducible p53-regulated death receptor gene" Nature Genetics, New York, NY, US, vol. 17, No. 2, Oct. 1997, pp. 141-143, XP 002083924.
Wu et al.: "Killer/DR5, a Novel DNA-Damage Inducible Death Receptor Gene, Linksthe P53-Tumor Suppressor to Caspase Activation and Apoptotic Death" Advances in Experimental Medicine and Biology, Spring St., NY, US, vol. 465, 2000, pp. 143-151, XP 001016228.
D. Hu et al.: "Characterization of Human Homologs of the *Drosophila* seven in absentia (sina) Gene". Genomics, vol. 46, No.1, Nov. 1997, pp. 103-111. Cited in the PCT search report.
G. Pan et al.: "An Antagonist Decoy Receptor and a Death Domain Containing Receptor for Trail", Science, vol. 227, Aug. 1997, pp. 815-818. cited in the PCT search report.
Edited by Shuichi Uenokawa et al.: Seibusu Kagaku Jikken'ho', Series (vol. 43), "Idenshi Hatsugen Kenkyoho". Japan Scientific Societies Press, Mar. 10, 2000, pp. 59-75. Cited in the PCT search report.
Certification by Japan DNA data bank, Mar. 22, 2001.
Alberts, B. et al., "Molecular Biology of The Cell", 1994, Third Edition, Garland Publishing, New York, NY, pp. 420-425.
Takimoto, R. et al., "Wild-type P53 transactivates the Killer/DR5 gene through an intronic sequence-specific DNA-binding site", 2000, Oncogene, Vol. 19: pp. 1735-1743.
Kennell, D. "Principles and Practices of Nucleic Acid Hybridization", 1971, Progr. Nucl. Acid Res. Mol. Biol., vol. 11: pp. 259-301.
Chung et al., Characterization of human homologs of the *Drosophila* seven in absentia (sina) gene. Genomics (1997), vol. 46, No. 1, pp. 103-111. Cited in the PCT search report.

* cited by examiner

*Primary Examiner* — Michael Burkhart
(74) *Attorney, Agent, or Firm* — Westerman, Hattori, Daniels & Adrian, LLP

(57) ABSTRACT

The inventors discovered for the first time the nucleotide sequence of the human DR5 gene promoter, the nucleotide sequence of the human Siah-1 gene promoter and what appear to be the core promoter regions thereof. The present invention further provides a screening method for substances which regulate promoter activity, comprising a step of bringing a test substance into contact with cells holding a vector which comprises this DNA together with a reporter gene ligated expressibly to this DNA, and a step of detecting changes in the expressed amount of the reporter gene due to contact with the test substance. This screening method is a method of very efficiently selecting anti-cancer drugs and the like.

18 Claims, 4 Drawing Sheets

(A)

(B)

DR5 GENE PROMOTER AND SIAH-1 GENE PROMOTER

INCORPORATED-BY-REFERENCE TO RELATED APPLICATIONS

This application is a divisional application of U.S. Ser. No. 10/491,622, filed Apr. 2, 2004 as a National Stage of PCT International Application Number PCT/IB02/04074, filed Oct. 4, 2002, and is based upon and claims the benefit of priority from the prior Japanese Application No. 2001-309179, filed on Oct. 4, 2001, the entire contents of all of which are incorporated by reference.

TECHNICAL FIELD

The present invention relates to promoters for DR5 and Siah-1 genes, which are tumor suppression-related genes inducing apoptosis in cancer cells, to methods for screening for substances which regulate the activity of these promoters, and to substances obtained by these screening methods which regulate promoter activity.

BACKGROUND ART p53 gene is a typical tumor suppressor gene which has been reported to be frequently mutated in human cancers. p53 protein is known to be capable of suppressing onset and progress of cancer by acting as a transcription factor to transcriptionally activate target genes. More specifically, it is believed that when a mutation occurs in the genes of a normal cell and it starts to become tumorigenesis, p53 protein arrests the cell cycle at the G1 anaphase and performs DNA repair during that time, or when repair is impossible it destroys the incipient cancerous cells by apoptosis (*Kotsu Igaku* 53 (5/6), 178-180, 1999).

DR5 (Death Receptor 5) is known as one protein whose transcription is induced by p53 protein and which is involved in p53-dependent apoptosis. DR5 induces apoptosis by binding a tumor necrosis factor (TNF)-related apoptosis-inducing ligand (TRAIL). DR4, DcR1, and DcR2 are also known as TRAIL receptors. DcR1 and DcR2 have TRAIL-binding regions but lack active intracellular death regions and therefore do not induce apoptosis. On the other hand, DR4 and DR5 include both TRAIL-binding regions and intercellular death regions, and they induce apoptosis through these intercellular death regions (*Science* 277, 815-818 (1997)). TRAIL exhibits selective toxicity for cancer cells over normal cells both in vitro and in vivo (*J. Biol. Chem.* 271, 12687-12690). This is attributed to the fact that DcRs of TRAIL receptor genes are expressed more dominantly in normal cells than in cancer cells.

Siah-1 (seven in absentia homologue-1) is known as another protein whose transcription is induced by p53 (*EMBO J.* 17, 2736-2747 (1998)). Siah-1 is activated by p53 protein to cause apoptosis and cell cycle arrest.

More specifically, the protease complex proteasome is involved in Siah-1-induced apoptosis and cell cycle arrest. The proteasome is an enzyme which recognizes ubiquitin in a ubiquitinated target protein and degrades the target protein. When Siah-1 binds to an enzyme part of which binds ubiquitin to a target protein, it activates the ubiquitin-binding enzyme and consequently promotes degradation of the target protein by the proteasome. One target protein of the proteasome is the β-catenin protein, and degradation of β-catenin protein induces suppression of Cyclin D1, Myc and other genes expression, resulting in apoptosis and cell cycle arrest. (*Genes Dev.* 11, 2701-2714 (1997), *Genes Dev.* 12, 1775-1780 (1998), *Mol. Cell* 7, 915-926 (2001)).

As described above, because activation of DR5 gene and Siah-1 gene at the transcription level induces apoptosis and cell cycle arrest, they play an important role in tumor suppression, and if substances could be found which activated transcription of these genes they would be extremely useful for cancer therapy.

DISCLOSURE OF THE INVENTION

It is an object of the present invention to provide promoters for the human DR5 gene and Siah-1 gene, methods for screening for substances which regulate the activity of these promoters, and substances obtained by such screening methods which regulate promoter activity.

To achieve these objectives, the inventors succeeded after much research in preparing a partial fragment of DR5 gene and a partial fragment of Siah-1 gene, and by using these fragments as probes to screen a human leukocyte genomic library, succeeded in isolating human DR5 gene promoter region and human Siah-1 gene promoter region. By preparing a series of deletion mutants for these promoter regions, they also discovered the regions that chiefly contribute to the promoter activity.

Moreover, the inventors discovered that by using reporter plasmids with these promoter regions inserted it was possible to rapidly and accurately screen for substances which can regulate expression of DR5 gene or Siah-1 gene.

The present invention was completed based on the aforementioned findings, and provides the following respective promoter regions of the DR5 gene and Siah-1 gene, methods for screening for substances which regulate the activity of these promoters, and substances obtained by these screening methods which regulate promoter activity.

Item 1. A DNA of (a) or (b) below, or DNA which hybridizes under stringent conditions with this DNA and which functions as promoter;

(a) a DNA comprising the nucleotide sequence of base numbers 1029-1034 or the nucleotide sequence of base numbers 1075-1080 of SEQ ID NO:1, or (b) a DNA comprising the nucleotide sequence of base numbers 1029-1034 or the nucleotide sequence of base numbers 1075-1080 together with the nucleotide sequence of up to 6 bases adjacent thereto and upstream therefrom and/or the nucleotide sequence of up to 6 bases adjacent thereto and downstream therefrom, of SEQ ID NO:1.

Item 2. A DNA of (c) or (d) below, or a DNA which hybridizes under stringent conditions with this DNA and which functions as promoter.

(c) a DNA comprising any of the nucleotide sequences below of SEQ ID NO:1, or (d) a DNA comprising any of the nucleotide sequences below together with the nucleotide sequence of up to 6 bases adjacent thereto and upstream therefrom and/or the nucleotide sequence of up to 6 bases adjacent thereto and downstream therefrom, of SEQ ID NO:1:

nucleotide sequences of base numbers 102-108, 133-143, 149-162, 174-183, 196-210, 208-221, 211-220, 212-226, 222-231, 263-269, 265-278, 296-302, 377-383, 370-376, 409-420, 430-440, 431-436, 457-470, 458-470, 482-492, 498-507, 499-503, 500-505, 528-534, 536-541, 537-542, 542-547, 549-561, 555-567, 553-560, 559-566, 575-587, 593-598, 598-610, 601-610, 614-619, 618-623, 642-648, 650-656, 657-662, 683-697, 700-707, 742-747, 774-779, 785-798, 788-792, 792-799, 795-801, 809-813, 814-825, 815-825, 861-867, 867-872, 867-873, 901-913, 901-904, 902-911, 915-923, 919-924, 924-939, 921-928, 926-933, 930-936, 948-957, 971-977, 972-978, 989-994, 1026-1035, 1029-1034, 1048-1057, 1075-1080, 1097-1103, 1106-1113, 1125-1133, 1169-1175, 1200-1209, 1153-1162, 1160-1169, 1160-1168, 1206-1305, 1209-1220, 1230-1238, 1297-1304, 1324-1331, 1366-1377, 1373-1380, 1373-1382, 1391-1398, 1421-1430, 1430-1342, 1334-1341, 1521-1530, 1583-1589, 1591-1600, 1590-1596, 1591-1600, 1593-1604, 1607-1614, 1608-1615, 1626-1636, 1626-1638, 1628-1637, 1629-1638, 1629-1641, 1630-1641.

Item 3. A DNA comprising at least one of the nucleotide sequences of base numbers 619-776, base numbers 777-1025 and base numbers 1026-1108 of SEQ ID NO:1, or a DNA which hybridizes under stringent conditions with this DNA and which functions as promoter.

Item 4. A DNA comprising the nucleotide sequence of base numbers 1-1108 of SEQ ID NO:1, or a DNA which hybridizes under stringent conditions with this DNA and which functions as promoter.

Item 5. A DNA comprising the nucleotide sequence of SEQ ID NO:1, or a DNA which hybridizes under stringent conditions with this DNA and which functions as promoter.

Item 6. A DNA of (e) or (f) below, or a DNA which hybridizes under stringent conditions with this DNA and which functions as promoter.

(e) a DNA comprising the nucleotide sequence of base numbers 2219-2224 of SEQ ID NO:2(CCCGCC), or (f) a DNA comprising the nucleotide sequence of base numbers 2219-2224 together with the nucleotide sequence of up to 6 bases adjacent thereto and upstream therefrom and/or the nucleotide sequence of up to 6 bases adjacent thereto and downstream therefrom, of SEQ ID NO:2.

Item 7. A DNA of (g) or (h) below, or a DNA which hybridizes under stringent conditions with this DNA and which functions as promoter.

(g) a DNA comprising any of the following nucleotide sequences of SEQ ID NO:2, or (h) a DNA comprising any of the following nucleotide sequences together with the nucleotide sequence of up to 6 bases adjacent thereto and upstream therefrom and/or the nucleotide sequence of up to 6 bases adjacent thereto and downstream therefrom, of SEQ ID NO:2:

nucleotide sequence of base numbers 95-104, 158-170, 272-278, 320-326, 362-368, 438-444, 568-575, 753-762, 1383-1391, 1438-1447, 1509-1515, 1613-1619, 1649-1660, 1715-1724, 1728-1737, 1789-1797, 1826-1832, 1889-1895, 2058-2069, 2074-2078, 2103-2107, 2209-2216, 2219-2224, 2302-2307, 2317-2324

Item 8. A DNA comprising the nucleotide sequence of base numbers 2035-2382 of SEQ ID NO:2, or a DNA which hybridizes under stringent conditions with this DNA and which functions as promoter.

Item 9. A DNA comprising the nucleotide sequence of SEQ ID NO:2, or a DNA which hybridizes under stringent conditions with this DNA and which functions as promoter.

Item 10. A method for screening for substances which regulate promoter activity, comprising a step of bringing a test substance into contact with cells containing a vector which comprises the DNA according to any of Items 1 to 9 together with a reporter gene capable of being expressed by this DNA, and a step of detecting changes in the expressed amount of the reporter gene due to contact with the test substance.

Item 11. A method for screening for substances which regulate promoter activity, comprising a step of introducing a test substance into cells containing a vector which comprises the DNA according to any of Items 1 to 9 together with a reporter gene capable of being expressed by this DNA, and a step of detecting changes in the expressed amount of the reporter gene due to introduction of the test substance.

Item 12. A method for screening for substances which regulate promoter activity, comprising a step of bringing a test substance into contact with the DNA according to any of Items 1 to 9, and a step of detecting a substance bound to this DNA.

Item 13. A method for screening for substances which regulate promoter activity, comprising a step of bringing a DNA-binding protein into contact with the DNA according to any of Items 1 to 9 with or without the presence of a test substance, and a step of detecting changes in the amount of binding of the DNA-binding protein to the DNA due to the presence of a test substance.

Item 14. A substance which regulates promoter activity obtained by the method according to any of Items 10 to 13.

Item 15. A vector comprising DNA according to any of Items 1 to 9 together with a reporter gene capable of being expressed by this DNA.

Item 16. Cells containing the vector of Item 15.

DETAILED DESCRIPTION OF THE INVENTION

Human DR5 Gene Promoter (Isolation of Promoter Region)

In order to obtain promoter DNA for human DR5 gene, the inventors synthesized the two oligonucleotides 5'CCGCAATCTCTGCGCCCACAAAATACACCG3' (SEQ ID NO:3) and 5' GTTTCAGCCCTTAAAGTAGATCGGGCATCG3' (SEQ ID NO:4) based on the human DR5 gene sequence (*Science* 277, 815-818 (1997)), and labeled these oligonucleotides with [γ-$^{32}$P] using T4 polynucleotide kinase. The labeled oligonucleotides were used as probes for screening a human leukocyte genomic λPS library (Mol. Bio. Tec., Gottinngen, Germany) to obtain a DNA fragment of about 10 kb which is considered to be DR5 promoter DNA. Moreover, a SacI-NcoI fragment of about 2.5 kbp from this DNA fragment was subcloned into pGVB2 (Nippon Gene Code No. 306-04831), and its nucleotide sequence was determined by an ABI PRISM 310 Genetic Analyzer using a Big Dye Terminator Cycle Sequencing Kit (ABI PRISM, PE Applied Biosystems).

Of this SacI-NcoI fragment, the nucleotide sequence of a part of the 3' end region containing the NcoI site is shown as SEQ ID NO:1. This fragment contains the coding region of exon 1 (base numbers 1225-1368 of SEQ ID NO:1) and part of intron 1 (base numbers 1369-1654 of SEQ ID) of human DR5 gene, and these sequences matched the reported nucleotide sequence of human DR5 gene (*Science* 277, 815-818 (1997)).

Next, to confirm whether the isolated DNA exhibits DR5 promoter activity, an approximately 2.5 kb NcoI-SacI fragment of the resulting DNA was subcloned into luciferase reporter plasmid pGVB2 (Nippon Gene Code No. 306-04831) and transfected into MCF-7 cells (National Institute of Health Sciences Cell Bank, JCRB0134) in which DR5 gene is constantly expressed, and luciferase activity of MCF-7 cell lysate measured after a fixed culture time. Lysate of MCF-7 cells containing the aforementioned plasmid exhibited luciferase activity, confirming that the NcoI-SacI fragment has promoter activity.

In other words, DNA comprising the nucleotide sequence of SEQ ID NO:1 or DNA which hybridizes under stringent conditions with this DNA and which functions as promoter is most desirable as the DR5 gene promoter of the present invention.

DNA consisting of the nucleotide sequence of SEQ ID NO:1 or DNA which hybridizes under stringent conditions with this DNA and which functions as promoter is especially desirable.

DNA having one or two or more bases substituted, deleted or added in DNA comprising the nucleotide sequence of SEQ ID NO:1 can be prepared by introduction of deletion using restriction enzyme or DNA exonuclease, introduction of mutation by site-specific mutagenesis, modification of the promoter sequence by PCR using mutant primer, direct introduction of synthetic mutant DNA and the like.

The promoter of the present invention may be prepared by known methods based on the nucleotide sequence of human DR5 gene. For example, as mentioned above, it can be obtained by a screening method with hybridization of a human genomic library using, as probe, an oligonucleotide synthesized based on the nucleotide sequence or base sequence of human DR5 gene; it can be also obtained by using the human genomic library as the PCR template, synthesizing the oligonucleotides of a sense primer corresponding to the vector DNA and an antisense primer corresponding to part of DR5 DNA, and combining them to perform PCR.

(Regions that Mainly Contribute to Promoter Activity)

The human DR5 gene promoter of the present invention may comprise at least a nucleotide sequence of (1) or (2) below, or a nucleotide sequence which hybridizes under stringent conditions with the DNA of such a nucleotide sequence and which has promoter activity. A nucleotide sequence which consists of at least a nucleotide sequence of (1) or (2) below or which hybridizes under stringent conditions with the DNA of such a nucleotide sequence and which has promoter activity is particularly desirable.

(1) The nucleotide sequence of base numbers 619-776, the nucleotide sequence of base numbers 777-1025 or the nucleotide sequence of base numbers 1026-1108 of SEQ ID NO:1.

It has been concluded from the following that these are regions which contribute to promoter activity. That is, a commercial kit was used to generate a series of 5'-deletion mutants of the promoter region from luciferase reporter plasmid pGVB2 ligated with the SacI-NcoI fragment which is the DR5 gene promoter region. These mutants were transiently transfected into MCF-7 cells, and luciferase activity of MCF-7 cell lysate was measured after a fixed culture time. The results showed that luciferase activity was significantly reduced by deletion of the region of base numbers 619-776, the region of base numbers 777-1025 or the region of base numbers 1026-1108 from SEQ ID NO:1. This indicates that transcription factor binding sites or enhancer sites necessary for promoter activity are present in these regions.

(2) Any of the following nucleotide sequences in SEQ ID NO:1, or a nucleotide sequence consisting of any of the following nucleotide sequences together with a nucleotide sequence of up to 6 bases adjacent to and upstream therefrom and/or a nucleotide sequence of up to 6 bases adjacent to and downstream therefrom, in SEQ ID NO:1.

Nucleotide sequences of base numbers 102-108, 133-143, 149-162, 174-183, 196-210, 208-221, 211-220, 212-226, 222-231, 263-269, 265-278, 296-302, 377-383, 370-376, 409-420, 430-440, 431-436, 457-470, 458-470, 482-492, 498-507, 499-503, 500-505, 528-534, 536-541, 537-542, 542-547, 549-561, 555-567, 553-560, 559-566, 575-587, 593-598, 598-610, 601-610, 614-619, 618-623, 642-648, 650-656, 657-662, 683-697, 700-707, 742-747, 774-779, 785-798, 788-792, 792-799, 795-801, 809-813, 814-825, 815-825, 861-867, 867-872, 867-873, 901-913, 901-904, 902-911, 915-923, 919-924, 924-939, 921-928, 926-933, 930-936, 948-957, 971-977, 972-978, 989-994, 1026-1035, 1029-1034, 1048-1057, 1075-1080, 1097-1103, 1106-1113, 1125-1133, 1169-1175, 1200-1209, 1153-1162, 1160-1169, 1160-1168, 1206-1305, 1209-1220, 1230-1238, 1297-1304, 1324-1331, 1366-1377, 1373-1380, 1373-1382, 1391-1398, 1421-1430, 1430-1342, 1334-1341, 1521-1530, 1583-1589, 1591-1600, 1590-1596, 1591-1600, 1593-1604, 1607-1614, 1608-1615, 1626-1636, 1626-1638, 1628-1637, 1629-1638, 1629-1641, 1630-1641.

It was concluded from the following that these regions comprise transcription factor binding sites essential for promoter activity. That is, binding potential of the nucleotide sequence of SEQ ID NO:1 to known transcription factors was investigated by a computer search using TFSEARCH. The known transcription factors that were used included GATA-1, AML-1a, c-Ets2, ADR1, c-Myb, SRY, Sp1, MZF1, CdxA, NFkB, p300, HSF2, Tst-1, Sox-5, Oct-1, GATA-1, Tst-1, Nkx-2, C/EBP β, deltaE, Ik-2, Elk-1, IRF-2, E47, SPY, STAT, USF, GATA-3, TATA, c-Rel and the like. The search revealed that all the DNA regions above are regions capable of binding with any of these transcription factors.

It is also possible that the adjacent DNA regions up to about 6 bases before and after these DNA regions may be involved in binding with transcription factors. That is, DNA comprising these nucleotide sequences together with the nucleotide sequences adjacent to and up to 6 bases upstream therefrom (particularly DNA consisting of these nucleotide sequences together with the nucleotide sequences adjacent to and up to 6 bases upstream therefrom) and DNA comprising these nucleotide sequences together with the nucleotide sequences adjacent to and up to 6 bases downstream therefrom (particularly DNA consisting of these nucleotide sequences together with the nucleotide sequences adjacent to and up to 6 bases downstream therefrom) and DNA comprising these nucleotide sequences together with the nucleotide sequences adjacent to and up to 6 bases upstream and downstream therefrom (particularly DNA consisting of these nucleotide sequences together with the nucleotide sequences adjacent to and up to 6 bases upstream and downstream therefrom) may also bind to transcription factors. "Up to 6 bases" includes cases in which there are 6 bases, 5 bases, 4 bases, 3 bases, 2 bases or 1 base.

Of the aforementioned regions having binding potential to transcription factors, the DNA region indicated by base numbers 1029-1034 and the DNA region indicated by base numbers 1075-1080 are thought to be core promoter regions. This is because these two potential transcription factor binding sites are the sites closest to the initiation codon of the DR5 gene, and because when a site-directed mutagenesis is introduced into these two sites in a luciferase reporter plasmid ligated with promoter DNA comprising these two potential transcription factor binding sites, the amount of luciferase expression declines significantly.

Consequently, of the DNA listed under (2) above as the DR5 gene promoter of the present invention, DNA comprising the nucleotide sequence of base numbers 1029-1034 or the nucleotide sequence of base numbers 1075-1080, or DNA comprising these nucleotide sequences together with the nucleotide sequences adjacent to and up to 6 bases upstream and/or adjacent to and up to 6 bases downstream therefrom is particularly preferable. DNA consisting of the nucleotide sequence of base numbers 1029-1034 or the nucleotide sequence of base numbers 1075-1080, or DNA consisting of these nucleotide sequences together with the nucleotide sequences adjacent to and up to 6 bases upstream and/or adjacent to and up to 6 bases downstream therefrom is even more preferable.

Human Siah-1 Gene Promoter (Isolation of Siah-1 Promoter Region)

In order to obtain human Siah-1 gene promoter DNA, the inventors synthesized the two oligonucleotides 5'GACGGAGCGCGTTGGTGCCAGGACCGGGGT3' (SEQ ID NO:5) and 5'TTCCCGGCGCCGAGACCGACGGGACACCCT3' (SEQ ID NO:6) comprising the DNA sequence of exon 1 of human Siah-1 gene based on the nucleotide sequence of human Siah-1 gene (*Genomics* 46, 103-111 (1997)), and labeled these oligonucleotides with [$\gamma$-$^{32}$P] using T4 polynucleotide kinase. The labeled oligonucleotides were used as probes for screening a human leukocyte genomic λPS library (Mol. Bio. Tec., Gottinngen, Germany) to obtain an approximately 16.5 kb SacI-SacI fragment comprising exon 1 of human Siah-1 gene and its 5'-flanking region. A 2515 by Kpn-1-NcoI fragment and this SacI fragment, whose NcoI site had been introduced by PCR, was subcloned into pGVB2 (Nippon Gene Code No. 306-04831), and its nucleotide sequence determined with an ABI PRISM 310 Genetic Analyzer using a Big Dye Terminator Cycle Sequencing Kit (ABI PRISM, PE APPLIED Biosystems).

The nucleotide sequence of this Kpn-1-NcoI fragment is shown in SEQ ID NO:2. This fragment includes the 5'-flanking region of the human Siah-1 gene (part of exon 1; base numbers 2388-2515 of SEQ ID NO:2), and this sequence matched the reported nucleotide sequence (*Genomics* 46, 103-111 (1997)) of the 5'-flanking region of human Siah-1 gene.

Next, in order to confirm that the isolated DNA exhibits Siah-1 promoter activity, luciferase reporter plasmid pGVB2 (Nippon Gene Code No. 306-04831) comprising the aforementioned 2515 by Kpn-1-NcoI fragment was transfected into MCF-7 cells in which Siah-1 gene is constantly expressed (National Institute of Health Sciences Cell Bank, JCRB0134), and luciferase activity of MCF-7 cell lysate measured after a fixed culture time. The results confirm that lysate of MCF-7 cells having the introduced plasmid exhibits luciferase activity, and that the Kpn-1-NcoI fragment has promoter activity.

That is, DNA comprising the nucleotide sequence of SEQ ID NO:2 or DNA which hybridizes under stringent conditions with this DNA and which functions as promoter is most preferable as the Siah-1 gene promoter of the present invention. DNA consisting of the nucleotide sequence of SEQ ID NO:2 or DNA which hybridizes under stringent conditions with this DNA and which functions as promoter is particularly preferable.

(Regions Which Mainly Contribute to Promoter Activity)

The promoter of the present invention may comprise at least a nucleotide sequence of (3) or (4) below, or a nucleotide sequence which hybridizes under stringent conditions with DNA of such a nucleotide sequence and which has promoter activity. The promoter consisting of a nucleotide sequence of (3) or (4) below, or a nucleotide sequence which hybridizes under stringent conditions with DNA of such a nucleotide sequence and which has promoter activity is preferable.

(3) The nucleotide sequence of base numbers 2035-2382 in SEQ ID NO:2

It has been concluded from the following that this is a region which contributes to promoter activity. That is, a series of 5'-end deletion mutants of the promoter region was prepared from luciferase reporter plasmid pGVB2 having ligated KpnI-NcoI fragment, which is the promoter region of the Siah-1 gene. These mutants were transiently transfected into MCF-7 cells, and the luciferase activity of the MCF-7 cell lysate measured after a fixed culture time. Deletion of the region of base numbers 2035-2382 from SEQ ID NO:2 resulted in a significant decrease in luciferase activity. It is believed that a transcription factor binding site or enhancer site essential for promoter activity is present in this region.

(4) Any of the following nucleotide sequences of SEQ ID NO:2, or any of the following nucleotide sequences together with up to 6 bases adjacent to and upstream therefrom and/or up to 6 bases adjacent to and downstream therefrom, in SEQ ID NO:2.

Nucleotide sequences of base numbers 95-104, 158-170, 272-278, 320-326, 362-368, 438-444, 568-575, 753-762, 1383-1391, 1438-1447, 1509-1515, 1613-1619, 1649-1660, 1715-1724, 1728-1737, 1789-1797, 1826-1832, 1889-1895, 2058-2069, 2074-2078, 2103-2107, 2209-2216, 2219-2224, 2302-2307, 2317-2324

It has been concluded from the following that these regions comprises transcription factor binding sites essential for promoter activity. That is, the potential binding of the nucleotide sequence of SEQ ID NO:2 to known transcription factors was investigated by means of a computer search using TFSEARCH. The known transcription factors GATA-1, C/EBP, SRY, cdxA, CREB, GATA2, GATA3, NFκB, Sp1, N-myc, v-Myb, E2F and the like were used. The results of the search showed that the above respective DNA regions had potential binding these transcription factors.

The adjacent DNA regions up to about 6 bases before and after these DNA regions may also contribute to binding transcription factors. That is, DNA comprising these nucleotide sequences together with the adjacent nucleotide sequences of up to 6 bases upstream therefrom (particularly DNA consisting of these nucleotide sequences together with the adjacent nucleotide sequences of up to 6 bases upstream therefrom), DNA comprising these nucleotide sequences together with the adjacent nucleotide sequences of up to 6 bases downstream therefrom (particularly DNA consisting of these nucleotide sequences together with the adjacent nucleotide sequences of up to 6 bases downstream therefrom) or DNA comprising these nucleotide sequences together with the adjacent nucleotide sequences of up to 6 bases upstream and downstream therefrom (particularly DNA consisting of these nucleotide sequences together with the adjacent nucleotide sequences of up to 6 bases upstream and downstream therefrom) also has potential binding to transcription factors.

Of the aforementioned transcription factor binding potential regions, the DNA region indicated by base numbers 2219-2224 is believed to be the core promoter region. This is deduced from the fact that when a site-directed mutagenesis is introduced into the DNA region indicated by base numbers 2219-2224 in a luciferase reporter plasmid ligated with promoter DNA comprising this DNA region, the amount of expressed luciferase is significantly lower.

Consequently, of the DNA listed under (4) above as the Siah-1 gene promoter of the present invention, DNA comprising the nucleotide sequence of base numbers 2219-2224 of SEQ ID NO:1 or DNA comprising this nucleotide sequence together with an adjacent nucleotide sequence up to 6 bases upstream therefrom and/or up to 6 bases downstream therefrom is particularly preferable. DNA consisting of the nucleotide sequence of base numbers 2219-2224 of SEQ ID NO:1 or DNA consisting of this nucleotide sequence together with an adjacent nucleotide sequence up to 6 bases upstream therefrom and/or up to 6 bases downstream therefrom is even more preferable.

Utility of Human DR5 Gene Promoter and Human Siah-1 Gene Promoter

The promoter DNA of the present invention can be used for treating or preventing DR5 or Siah-1 protein deficiency, abnormal expression or the like due to mutations in vivo. That is, DR5 protein or Siah-1 protein can be expressed under normal control by inserting DR5 gene having the DR5 promoter DNA of the present invention or Siah-1 gene having the Siah-1 promoter of the present invention into a retrovirus, adenovirus, adeno-associated virus or other vector, or including it in a liposome or the like and introducing it into somatic cells, as a means of improving DR5 protein or Siah-1 protein deficiency, abnormal expression or the like.

If it is found that the promoter DNA of the present invention is activated or suppressed by a specific stimulus, it will be possible to induce or suppress expression of a desired gene by constructing and introducing into somatic cells a vector or the like with the DNA of the present invention inserted upstream from the desired gene, and applying the stimulus. For example, using a cytocidal gene as the desired gene, it is possible to selectively kill cells having the introduced promoter DNA of the present invention by specifically simulating the gene. Thus, such use of the promoter DNA of the present can be applied to a wide range of decease such as cancer and the like, in which cells need to be killed.

Moreover, DNA having the same nucleotide sequence as the promoter DNA of the present invention can competitively block binding of cellular DR5 promoter DNA or Siah-1 promoter DNA with proteins capable of binding to these promoters such as transcription factors. Thus, if the DNA competitively blocks binding of DR5 or Siah-1 promoter to a protein which inhibits the promoter activity of DR5 or Siah-1 promoter DNA, this method can be used to stimulate DR5 or Siah-1 promoter activity. On the other hand, if it competitively blocks binding of DR5 or Siah-1 promoter to a protein which stimulates promoter activity, this method can be used to inhibit DR5 or Siah-1 promoter activity.

As mentioned above, since DR5 or Siah-1 protein has the effect of causing apoptosis or cell cycle arrest, stimulation of DR5 or Siah-1 promoter activity is useful in the treatment of cell proliferation disorders including malignant tumors, arteriosclerosis, restenosis due to proliferation of the vascular endothelial cells following balloon coronary angioplasty, and the like. On the other hand, suppression of DR5 or Siah-1 promoter DNA activity is useful in the treatment of disorders in which cell proliferation is needed, such as aplastic anemia, cirrhosis of the liver, myocardial infarction, cerebral infarction, wound healing, and the like.

In addition, as described below, the promoter DNA of the present invention can be used to screen substances which regulate promoter activity, through the use of reporter genes which can be expressed by this DNA. That is, the promoter DNA of the present invention can be used to screen substances which can regulate DR5 or Siah-1 gene at the transcription level when they act on the promoter DNA either directly by binding to the promoter DNA or indirectly by binding to a cell membrane receptor or intercellular protein.

Compounds which can transcriptionally activate DR5 or Siah-1 gene are useful in the treatment of cell proliferation disorders including malignant tumors, arteriosclerosis, restenosis due to proliferation of the vascular endothelial cells following balloon coronary angioplasty, and the like. On the other hand, substances which can transcriptionally suppress DR5 or Siah-1 gene are effective in the treatment of disorders in which cell proliferation is needed, such as aplastic anemia, cirrhosis of the liver, myocardial infarction, cerebral infarction, wound healing and the likes.

Method for Screening for Substances Which Regulate DR5 or Siah-1 Gene Promoter Activity
(Test Substances)

In the screening methods of the present invention, there are no particular limits on the test substance, and the test substances include a wide range of proteins, oligopeptides, DNAs encoding them, polysaccharides, low molecular weight compounds and the like. These may be isolated from nature or synthesized artificially. There are no particular limits on the kinds of such substances or their molecular weights, but from the standpoint of movement into cells, low molecular weight compounds are the most preferable.

If an oligopeptide or protein is one which moves into cells to act on the promoter of the present invention, it may be used as a fused protein with a membrane permeable protein for therapeutic drug applications, with the membrane permeable mechanism of the membrane permeable protein being exploited to move it into the cells.
(Reporter Genes)

A wide range of known reporter genes can be used as reporter gene used in the screening methods described below. Examples of known reporter genes include the luciferase gene, chloramphenicol-acetyl-transferase (CAT) gene, secretory alkaliphosphatase (SEAP), human growth hormone (hGH), β-glucuronidase (GUS), green fluorescent protein (GFP) and the like. Of these, the luciferase gene is most preferable because it is highly sensitive and its activity is easily measured.

These are sold commercially as reporter plasmids lacking an intrinsic promoter region or reporter plasmids lacking an intrinsic enhancer region. Commercially available luciferase plasmids include pT811uc, pS1uc2, pXP1/pXP2 (all Nordeen, 1988) and the like.

A commercial reporter plasmid can be used for the reporter gene, or it can be used being inserted into a known vector. A plasmid vector, virus vector or the like may be used as vector. The vector for transfecting animal cells is preferable.

Animal cell vectors that can be used include for example pUC18, pUC19, M13mp18, pBluescript, pBR322 and the like.

When measuring the expressed amount of the reporter gene, in the case of SEAP and hGH, among the reporter proteins, the amount of protein expressed in cell culture supernatant can be measured because they are secretory proteins, while for the other reporter proteins, the amount of expressed protein in a lysate of cells lysed with a surfactant or the like can be measured by a method suited to those proteins.

The expressed amount of luciferase gene can be measured by using a luminometer to detect fluorescence in cell lysate due to degradation of luciferin, which is catalyzed by luciferase. Fluorescence emitted by cells can also be detected using a luminometer.

These reporter assays can be performed manually, but they can also be performed rapidly and easily using high throughput screening (Soshiki Baiyo Kogaku (Tissue Culture Engineering) Vol. 23, No. 13, 521-524, U.S. Pat. No. 5,670,113), which is done automatically with a machine.
(First Screening Method of the Present Invention)

The first screening method of the present invention comprises a step of bringing a test substance into contact with cells holding a vector comprising DNA which includes the human DR5 or Siah-1 gene promoter region of the present invention (here and below, this may be a region comprising the minimum region required for promoter activity) and a reporter gene ligated expressibly to this DNA, and a step of detecting changes in the amount of expressed reporter gene due to contact with the test substance.

When screening for a substance which activates DR5 promoter, the cells used may be cells in which DR5 gene itself is normal but DR5 protein activity is reduced. When screening for a substance which activates Siah-1 promoter, cells may be used in which Siah-1 protein activity is reduced. Specifically, cancer cells such as human osteosarcoma cell line Saos-2 (ATCC, HTB85), colon cancer cell line DLD-1, human breast cancer cell line MCF-7 (National Institute of Health Sciences Cell Bank, JCRB0134), human renal epithelial cell line 293 (ATCC, CRL1573), erythroleukemia cell line K562 (ATCC, CCL243) and the like which have recognized p53 mutations can be used.

When screening for substances which suppress such promoter activity, cells can be selected from a wide range of known cells such as Vero cells, HeLa cells, CV1 cells, Namalva cells, COS1 cells, CHO cells and the like.

The vector comprising a promoter region of the present invention and a reporter gene ligated so that it can be expressed by this promoter is as explained above. This vector is preferably introduced constantly into cells.

Contact of cells with the test substance can be accomplished for example as follows. Namely, cells holding the vector are passaged in a suitable medium for those cells, and cultured so that they reach the logarithmic growth phase. For contact with the test substance, the cells are seeded to about 20-30% confluence, and cultured for about 24 hours. Next, the test substance is added to the cell culture to a concentration of about 5 nM-50 µM. They are then incubated at about 37° C. for about 12-48 hours or preferably about 24 hours. A caspase inhibitor may be added in order to prevent the test substance from activating the promoter and inducing apoptosis.

Next, the expressed amount of reporter gene can be measured by a method suited to the type of reporter gene. For example, when using the luciferase gene as reporter gene, the cells can be lysed in a solvent containing a surfactant, and luciferase activity in the lysate can be measured by using a luminometer to detect luminescence due to degradation of luciferin.

When application of a test substance results in luciferase activity of about 50% or less that of the control, the promoter is considered suppressed. If luciferase activity is 200% or more that of the control, the promoter is considered activated.

There are no particular limits on the test substance of this method, and a wide range of proteins, oligopeptides, polysaccharides, low molecular weight compounds and the like can be used.

With this method, substances can be selected which affect activity of the promoter DNA of the present invention indirectly through cell membrane receptors or the like, as well as low molecular weight compounds which enter the cells and bind directly to the promoters of the present invention, and low molecular weight compounds which enter the cells and act indirectly on the promoters of the present invention by acting on intracellular proteins.

(Second Screening Method of the Present Invention)

The second screening method of the present invention is a method comprising a step of introducing a test substance into cells holding a vector comprising DNA which includes the promoter region of the human DR5 or Siah-1 gene promoter region of the present invention and a reporter gene ligated expressibly to this DNA, and a step of detecting changes in the expressed amount of reporter gene due to contact with the test substance.

In the second screening method, the cells and vectors and the methods for measuring the expressed amount of reporter gene are the same as for the first screening method.

As an example of this method, a test substance can be temporarily introduced into the aforementioned cells by a method normally used for transfection such as the calcium phosphate method, DEAE-dextran method, electroporation method or liposome method, and changes can be detected in the expressed amount of reporter gene.

If the test substance is a protein, it can be introduced into cells as a fused protein together with a membrane permeable protein.

With this method, it is possible to obtain not only substances which bind directly to the promoter DNA of the present invention, but also substances which regulate the activity of the promoter DNA of the present invention indirectly by acting on intrinsic proteins or the like in the cells. The test substances screened by this method may include not only DNA but also proteins, oligopeptides, polysaccharides, low molecular weight compounds and the like.

The one-hybrid method can be given as another example of this method. Specifically, a reporter plasmid with the promoter DNA of the present invention inserted is introduced stably into cells, a gene library is then introduced therein, and proteins and the like which bind to the promoter DNA of the present invention are selected by selecting clones which exhibit promotion or suppression of reporter gene expression. With this method it is possible to obtain not only proteins and the like which bind directly to the promoter DNA of the present invention, but also proteins and the like which regulate the activity of the promoter DNA of the present invention indirectly by acting on intrinsic proteins and the like in the cells. The one-hybrid method (Li J. J. and Herskowitz I., Science 262:1870-1873 (1993); Wang M. M. and Reed R. R., Nature 364:121-126 (1993)) can be carried out for example using a commercial kit such as the "Matchmaker System" (ClONTECH).

(Third Screening Method of the Present Invention)

The third screening method of the present invention is a method comprising a step of bringing a test substance into contact with a DNA fragment comprising the human DR5 or Siah-1 gene promoter region of the present invention, and a step of detecting the substance bound to this DNA.

In the third screening method, a promoter DNA fragment of normally 6 by or more and preferably 18 by or more can be used.

Affinity purification can be given as one example of this method. Specifically, the promoter DNA of the present invention is biotinylated and bound to magnetic beads having bound streptoavidin to prepare DNA affinity beads. Next, these are incubated with the test substance, and test substances which bind specifically to the promoter DNA of the present invention are purified and their structures are determined.

In this method there are no particular limits on the test substance, which may be from a wide range including proteins, oligopeptides, polysaccharides, low molecular weight compounds and the like. For example, as a mixture of natural proteins or oligopeptides (here and below, "proteins and the like"), a cell nucleus extract, microorganism culture supernatant and the like can be used. A nucleus extract is preferable because it includes a DNA binding protein such as a transcription factor. When using a mixture of proteins or the like, it is possible to obtain not only test substances which bind directly to the promoter DNA of the present invention, but also proteins and the like which have no DNA binding ability but bind indirectly to the promoter DNA of the present invention by forming complexes with DNA-binding proteins and the like.

When the test substance is a protein or the like, Southwestern blotting can be given as another example of this method. Specifically, a mixture of a protein or the like isolated by SDS-PAGE is transferred to a filter membrane and blotted directly with the promoter DNA of the present invention as probe, and protein or the like which binds to the DNA probe is selected.

Another specific example of Southwestern blotting is a method wherein a protein or the like is expressed in *E. coli* having an introduced gene library, then transferred to a filter membrane and blotted directly with the promoter DNA of the present invention as a probe, clones expressing the protein or the like are selected which bind to the DNA probe, and the genes encoding the protein are isolated. With this method it is possible to obtain both proteins or the like having binding activity with the DNA of the present invention and genes encoding the proteins.

Yet another example of this method is the gel shift method which is used when the test substance is a protein or the like. Specifically, a mixture of a protein or the like is mixed with a promoter DNA probe of the present invention labeled with an isotope or the like, it is subjected to polyacrylamide gel electrophoresis, and the bands of complexes of the protein or the like with the promoter DNA of the present invention in polyacrylamide gel are detected by the gel shift method. With this method it is possible to detect both proteins or the like which bind directly to the promoter DNA of the present invention and proteins or the like which bind indirectly to the promoter DNA of the present invention by binding with this protein or the like.

(Fourth Screening Method of the Present Invention)

The fourth screening method of the present invention comprises a step in which DNA-binding protein is brought into contact with a DNA fragment comprising the human DR5 or Siah-1 gene promoter region of the present invention in the presence or in the absence of a test substance, and a step in which differences in the amount of binding of the DNA-binding protein to the DNA depending on the presence or absence of the test substance are detected.

There are no particular limits on substances screened by this method, and a wide range of proteins, oligopeptides, polysaccharides, low molecular weight compounds and the like can be used.

Transcription factors and other proteins which are expected from a computer search to bind to the promoter DNA fragments used for screening can be used as the DNA-binding protein.

The gel shift method explained above can be given as an example of this method. Specifically, a DNA-binding protein and a labeled promoter DNA probe are bound together in the presence or in the absence of a test substance, and substances selected which either promote or suppress formation of the band for a composite of the DNA-binding protein and the promoter DNA of the present invention. In this way it is possible to select substances which do not directly bind to the promoter of the present invention but which promote or suppress binding of DNA-binding protein to promoter DNA. For example, if a protein or the like which binds to the promoter DNA of the present invention is one which inhibits the activity of the promoter DNA of the present invention in the body, it is considered that a substance which inhibited binding of this protein or the like with the promoter DNA of the present invention can promote the activity of the promoter DNA of the present invention.

The following method can be given as another example of this method. Namely, a protein is purified having glutathione S-transferase fused with a DNA-binding protein which is expected to bind to the promoter DNA of the present invention, the fused protein is bound to microplates covered with anti-glutathione S-transferase antibody, biotinylated promoter DNA of the present invention is brought into contact with the fused protein, and binding of the fused protein to the promoter DNA of the present invention is detected streptavidinated alkaliphosphatase. When adding the promoter DNA of the present invention, the test substance is also added, and substances are selected which promote or suppress binding of the fused protein to the promoter DNA of the present invention.

With this method it is possible to obtain both substances which act directly on the promoter DNA of the present invention and substances which act on the DNA-binding protein. For example, if a protein which binds to the promoter DNA of the present invention inhibits the activity of the promoter DNA of the present invention in the body, a compound which inhibits binding of this protein to the promoter DNA of the present invention is considered to be capable of promoting the activity of the promoter DNA of the present invention.

Substances Obtained by the Screening Methods

A substance obtained by the aforementioned screening methods can be used as drug in the following forms.

Namely, it can be used alone or prepared as a pharmaceutical composition by mixing with pharmacologically acceptable carriers (including excipients, extenders, binders, lubricants and the like) or conventional additives. This pharmaceutical composition can be administered orally or parenterally depending on the form of preparation (tablets, pills, capsules, powders, granules, syrup or other orally administered form, injectable solution, drops, external preparation, suppository or other parenterally administered form) or the like. The dosage will differ depending on the type of active constituent, administration route, subject of administration and patient age, weight, symptoms and the like and cannot be stipulated uniformly, but can be determined easily by a person having ordinary skill in the field.

When the substance obtained is an oligopeptide or protein, it can be administered as a protein fused together with a membrane permeable protein. In this way, the oligopeptide or protein can be transported into the cell by exploiting the membrane permeable mechanism of the membrane permeable protein. DNA encoding this oligopeptide or protein can also be incorporated into a virus vector for gene therapy and introduced into the target cells. In these cases, the dosage and administration method will differ depending on the patient age, weight, symptoms and the like and cannot be stipulated uniformly, but can be determined easily by a person having ordinary skill in the field.

When the substance obtained is a polynucleotide or oligonucleotide, it can be administered as drug in the form of the aforementioned pharmaceutical composition, or it can for example be enclosed in a liposome and introduced into cells by means of a liposome delivery system, microinjection, direct injection or a gene gun. In these cases as well, the dosage and administration method will differ depending on the patient age, weight, symptoms and the like and cannot be stipulated uniformly, but can be selected appropriately by a person having ordinary skill in the field. Moreover, it can also be incorporated into a virus vector for gene therapy or the like for introduction into the target cells.

If the obtained substance is one which increases the expressed amount of DR5 gene or Siah-1 gene, a drug having the substance as its active ingredient is useful as a therapeutic or preventative drug for cell proliferation disorders such as malignant tumors, arteriosclerosis and restenosis due to proliferation of the vascular endothelial cells following balloon coronary angioplasty. On the other hand, if the obtained substance is one which decreases the expressed amount of DR5 gene or Siah-1 gene, a drug having the substance as its active ingredient is useful as a therapeutic or preventative drug for disorders in which cell proliferation is needed, such as aplastic anemia, cirrhosis of the liver, myocardial infarction, cerebral infarction and wound healing.

Effects of the Invention

Promoters for the tumor suppression-related genes human DR5 gene and human Siah-1 gene are provided by the present invention, thus allowing the activity of these promoters to be regulated and compounds which control expression of DR5 gene and Siah-1 gene to be screened.

As mentioned above, p53 protein induces transcription of DR5 gene and Siah-1 gene, and contributes to suppressing cancer by causing apoptosis and cell cycle arrest. Because it seems that the expressed amount of DR5 and Siah-1 is often reduced in cancer cells rather than the proteins themselves being inactivated, a substance that could activate DR5 or Siah-1 gene at the transcription level by acting directly or indirectly on the promoters of the present invention is extremely useful for treating cancer and the like.

Moreover, substances which act on DR5 and Siah-1 gene promoters hold great potential for selective toxicity towards cancer cells. That is, because the promoter activity of tumor suppression-related genes such as DR5 and Siah-1 is normal in normal cells, administration of a substance which activates such promoters is unlikely to increase promoter activity any further, but because the promoter activity of these tumor suppression-related genes is suppressed in cancer cells, promoter activity can be raised to a normal level through administration of the substance. Consequently, substances which activate the DR5 promoter and Siah-1 promoter hold great potential for selective toxicity towards cancer cells.

Hitherto known cancer therapy through gene introduction has suffered from such problems as low efficiency of transfection into cells, the need for local administration, risk of side-effects from the virus vector and risk of genetic disease when the gene is introduced into reproductive cells, but these problems can be resolved by using a substance which regulates the target gene at the transcription level by regulating promoter activity. Two particular advantages are the possibility of remote administration and high efficiency of introduction into cells.

EXAMPLES

The present invention is explained in more detail below using examples, but the present invention is not limited to these examples.

First, the DR5 gene promoter of the present invention and the regions essential for its promoter activity are explained in detail, and next the nucleotide sequence of the Siah-1 gene promoter and the regions essential for its promoter activity are explained in detail.

Example 1

Cells Used

Human breast cancer cell line MCF-7 (National Institute of Health Sciences Cell Bank, JCRB0134), human renal epithelial cell line 293 (ATCC, CRL1573) and human osteosarcoma cell line Saos-2 (ATCC, HTB85) were maintained in Dulbecco's modified Eagle medium (DMEM, Japan, Tokyo, Nissui, Code No. 05919) with 10% fetal calf serum, and incubated at 37° C. in a humidified atmosphere containing 5% $CO_2$. Erythroleukemia cells K562 (ATCC, CCL243) were maintained in RPMI 1640 medium (Japan, Tokyo, Nissui, Code No. 05918) with 10% fetal bovine serum, and incubated in the same way.

Example 2

Cloning of Human DR5 Gene Promoter DNA

Two oligonucleotides (CCGCAATCTCTGCGCCCA-CAAAATACACCG and GTTTCAGCCCTTAAAGTA-GATCGGGCATCG) were synthesized based on the human DR5 nucleotide sequence (Science 277, 815-818 (1997)), and used as probes for screening a human leukocyte genomic library. These probes were labeled with [$\gamma$-$^{32}$P]ATP (Amersham Pharmacia Biotech, UK, Certificate No. 945784) and T4 polynucleotide kinase (Japan, Osaka, Toyobo, PNK-103). Labeling conditions were according to the manual for the T4 polynucleotide kinase. Approximately $3.8 \times 10^6$ phage plaques of a human leukocyte genome-derived $\lambda$PS library (Mol. Biol. Tec., Germany, Product No. OB-4901-00, Funakoshi Catalogue) were screened using these probes in order to obtain genomic DNA fragments comprising the 5'-flanking region of human DR5 gene. Screening was performed according to the manual for the $\lambda$PS library. Hybridization was performed for at least 16 hours at 50° C. in a buffer solution containing 5×SSC, 0.1% SDS, 5× Denhart's solution and 0.1 $\mu$g/$\mu$l heat-denatured fish sperm DNA. One positive phage plaque was converted to a plasmid according to the manual for the $\lambda$PS genome library (Mol. Biol. Tec., Germany, Product No. OB-4910-10, Funakoshi Catalogue), and its DNA was amplified and purified. Specifically, a single colony was grown overnight in LB broth, and plasmid DNA was extracted and purified using a QIAGEN kit (QIAGEN plasmid maxi kit (25), Cat. No. 12163, Germany).

The genomic DNA fragment was treated with SacI, NcoI (Japan, Toyobo) and other restriction enzymes, and analyzed by Southern blotting (Laboratory Manual Genetic Engineering, Third Edition, Ed. Masami Muramatsu, pp. 73-76).

Example 3

Nucleotide Sequence of Human DR5 Promoter DNA

An approximately 2.5 kb SacI-NcoI fragment derived from the positive phage DNA obtained in Example 2 was subcloned to pGVB2, and its nucleotide sequence was determined with an ABI PRISM 310 Genetic Analyzer using a Big Dye Terminator Cycle Sequencing Kit (ABI PRISM, PE APPLIED Biosystems, Lot No. 9805010, Part No. 4303152).

A sequence of 1654 bases including the 3' end of this 2.5 kb SacI-NcoI fragment is shown by SEQ ID NO:1. This sequence includes part of exon 1 and the 5'-flanking region of DR5 gene, with the nucleotide sequence of part of exon 1 being identical to the reported sequence of human DR5 gene (Science 277, 815-818 (1997)).

Example 4

Human DR5 Promoter Transcription Initiation Sites

In order to determine the transcription initiation sites, an RNA probe was prepared with T7-RNA polymerase (MAXI script, Ambion) using, as template, a fragment (SmaI-ApaI fragment) comprising exon 1 of DR5 genome DNA subcloned into pBluescript. Total RNA was also prepared from MCF-7 cells using Sepasol RNA I (Japan, Kyoto, nacalaitesque Code No. 30655-36). The RNA protection assay was carried out using an RPA III kit (Ambion) in accordance with the attached manual. The nucleotide sequence of the resulting product was determined using a T7 Sequencing Kit (Amersham Pharmacia Biotech).

As a result, it was determined that the C residue of base number 1076 and the A residue of base number 1102 in SEQ ID NO:1 are the transcription initiation sites.

Example 4

Search for Candidate Transcription Factor Binding Sites

The 5'-flanking region (nucleotide sequence shown in sequence table) of DR5 gene was searched with a computer by TFSEARCH for potential binding to known transcription factors. The transcription factors used in the search were GATA-1, AML-1a, c-Ets2, ADR1, c-Myb, SRY, Sp1, MZF1, CdxA, NFkB, p300, HSF2, Tst-1, Sox-5, Oct-1, GATA-1, Tst-1, Nkx-2, C/EBPβ, deltaE, Ik-2, Elk-1, IRF-2, E47, SPY, STAT, USF, GATA-3, TATA and c-Rel.

As a result, several nucleotide sequences were identified which may bind to known transcription factors. These are the nucleotide sequences shown by base numbers 102-108, 133-143, 149-162, 174-183, 196-210, 208-221, 211-220, 212-226, 222-231, 263-269, 265-278, 296-302, 377-383, 370-376, 409-420, 430-440, 431-436, 457-470, 458-470, 482-492, 498-507, 499-503, 500-505, 528-534, 536-541, 537-542, 542-547, 549-561, 555-567, 553-560, 559-566, 575-587, 593-598, 598-610, 601-610, 614-619, 618-623, 642-648, 650-656, 657-662, 683-697, 700-707, 742-747, 774-779, 785-798, 788-792, 792-799, 795-801, 809-813, 814-825, 815-825, 861-867, 867-872, 867-873, 901-913, 901-904, 902-911, 915-923, 919-924, 924-939, 921-928, 926-933, 930-936, 948-957, 971-977, 972-978, 989-994, 1026-1035, 1029-1034, 1048-1057, 1075-1080, 1097-1103, 1106-1113, 1125-1133, 1169-1175, 1200-1209, 1153-1162, 1160-1169, 1160-1168, 1206-1305, 1209-1220, 1230-1238, 1297-1304, 1324-1331, 1366-1377, 1373-1380, 1373-1382, 1391-1398, 1421-1430, 1430-1342, 1334-1341, 1521-1530, 1583-1589, 1591-1600, 1590-1596, 1591-1600, 1593-1604, 1607-1614, 1608-1615, 1626-1636, 1626-1638, 1628-1637, 1629-1638, 1629-1641 and 1630-1641 in SEQ ID NO:1.

These are regions which are expected to activate or inhibit transcription of DR5 by binding with specific substances.

Example 5

Confirming Promoter Activity and Determining Regions that Principally Contribute to Promoter Activity Example 5-1

An approximately 2.5 kb SacI-NcoI fragment comprising the DR5 promoter region obtained in Example 2 was subcloned into the SacI-NcoI site of luciferase reporter plasmid pGVB2 (Japan, Tokyo, Nippon Gene). This plasmid was named pDR5/SacI.

A series of 5'-deletion mutants of the promoter region of this invention was generated from pDR5/SacI using a "Kilo-sequence Deletion Kit" (Japan, Tokyo, Takara). These mutants are pDR5/37 comprising base numbers 37-1223, pDR5/619 comprising base numbers 619-1223, pDR5/777 comprising base numbers 777-1223, pDR5/1026 comprising base numbers 1026-1223, pDR5/1109 comprising base numbers 1109-1223 and pDR5/1186 comprising base numbers 1186-1223 in the sequence table.

These plasmids were transiently transfected into MCF-7 cells.

Specifically, MCF-7 cells ($3 \times 10^4$) were seeded in 12-well tissue culture plates, and after 24 hours, 0.5 µg of the aforementioned plasmid was transiently transfected into the cells together with 0.4 µg of pActβ-gal containing the actin promoter-regulated β-galactosidase gene co-transfected in order to standardize transfection efficiency, using a Cell Phect Transfection kit (Amersham Pharmacia Biotech, 27-9268-01). After 48 hours, luciferase activity in cell lysate was measured according to the protocols of a Pica Gene luminescence kit (Toyo Ink, Tokyo, Japan, Code No. 309-04321), and standardized by β-galactosidase activity in the cell lysate (Molecular Cloning 16. 66: Assay for β-galactosidase in extracts for mammalian cells (1986)). Each experiment was repeated three times, and each luciferase assay was triplicated. Significance was tested using a Student's t-test, and differences were considered significant when $p<0.05$.

The results are shown in FIG. 1. As shown in FIG. 1, cells transfected with plasmid pDR5/SacI having the full-length DR5 promoter demonstrated extremely strong luciferase activity, confirming that the DNA shown by SEQ ID NO:1 is the DR5 gene promoter region.

There were no significant differences in luciferase activity between plasmid pDR5/SacI having the full-length DR5 promoter and pDR5/37 and between pDR5/37 and pDR5/619, but significant differences between pDR5/619 and pDR5/777, between pDR5/777 and pDR5/1026, and between pDR5/1026 and pDR5/1109. The luciferase activity of cells having pDR5/1109 or pDR5/1186 was virtually the same as that of cells holding pGVB2 with no inserted promoter region.

From this it appears that transcription factor binding sites or enhancer sites essential for promoter activity of DR5 gene are present between base numbers 619-776, between base numbers 777-1025 and between base numbers 1026-1108 of SEQ ID NO:1.

Example 5-2

Next, of the sites shown in Example 4 to be candidate transcription factor binding sites, site-specific mutagenesis was performed at the two sites upstream from and closest to the initiation codon (regions of base numbers 1029-1034 and 1075-1080 in the sequence table (Sp1 sites)).

Specifically, pDR5mSp1-1 having an introduced substitution mutation in the region of base numbers 1029-1034 and pDR5mSp1-2 having an introduced substitution mutation in the region of base numbers 1075-1080 were prepared from luciferase reporter plasmid pDR5/1026 having inserted base numbers 1026-1223 of SEQ ID NO:1, using a QuickChange Site-Directed Mutagenesis Kit (Stratagene). In the same way, pDR5mTATA was prepared having an introduced substitution mutation in the TATA-like sequence of base numbers 1097-1103 in the sequence table. As in Example 5-2, the mutated reporter plasmids were transiently transfected into MCF-7 cells, and luciferase activity of the cell lysate was measured.

The nucleotide sequence and luciferase activity of each of the mutants are shown in FIGS. 2(A) and 2(B). From FIG. 2(B), it is clear that within the sequence of base numbers 1026-1223 (promoter region included in pDR5/1027) of SEQ ID NO:1 which contributes to promoter activity, the two Sp1 regions contribute chiefly to promoter activity, and that transcription binding sites or enhancer sites are present therein.

It is also clear that the TATA-like sequence of base numbers 1097-1103 in the sequence table does not contribute to promoter activity.

Example 6

Cloning of Human Siah-1 Gene Promoter DNA

Two oligonucleotides (5'GACGGAGCGCGTTGGTGC-CAGGACCGGGGT3' and 5'TTCCCGGCGCCGAGAC-CGACGGGACACCCT3') were synthesized based on the human Siah-1 sequence (*Genomics* 46, 103-111 (1997)), and used as probes for screening a human leukocyte genomic library. These probes were labeled with [γ-$^{32}$P]ATP (Amersham Pharmacia Biotech, UK, Certificate No. 945784) and T4 polynucleotide kinase (Japan, Osaka, Toyobo, PNK-103). Labeling conditions were according to the manual for the T4 polynucleotide kinase. Approximately $3.8\times10^6$ phage plaques of a human leukocyte genome-derived λPS library (Mol. Biol. Tec., Germany, product No. OB-4901-00, Funakoshi Catalogue) were screened using these probes in order to obtain genomic DNA fragments containing the 5'-flanking region of human Siah-1 gene. Screening was performed in accordance with the manual for the λPS phage genomic library. Hybridization was performed overnight at 50° C. in a buffer solution containing 5×SSC, 0.1% SDS, 5× Denhart's solution and 0.1 µg/µl heat-denatured fish sperm DNA. One positive phage plaque was converted to a plasmid according to the manual for the λPS genomic library, and its DNA was amplified and purified. Specifically, a single colony was grown overnight in LB broth, and plasmid DNA was extracted and purified using a QIAGEN kit (QIAGEN plasmid maxi kit (25), Cat. No. 12163, Germany).

The genomic DNA fragment was treated with KpnI, SacI, (Japan, Toyobo) and other restriction enzymes, and analyzed by Southern blot analysis (Laboratory Manual Genetic Engineering, Third Edition, Ed. Masami Muramatsu, pp. 73-76) using the oligonucleotides Siah-a and Siah-b.

Example 7

Nucleotide Sequence of Human Siah-1 Promoter DNA)

An approximately 2515 by KpnI-NcoI fragment derived from the positive phage DNA obtained in Example 6 was subcloned into pGVB2, and its nucleotide sequence was determined with an ABI PRISM 310 Genetic Analyzer using a Big Dye Terminator Cycle Sequencing Kit (ABI PRIMS, PE APPLIED Biosystems, Lot No. 9805010, Part No. 4303152). The nucleotide sequence is shown in SEQ ID NO:2.

This fragment comprises a 5'-flanking region (part of exon 1, base numbers 2388-2515 in SEQ ID NO:2) of human Siah-1 gene, and these sequences match the reported nucleotide sequence of the 5'-flanking region of human Siah-1 gene (*Genomics* 46, 103-111 (1997)).

Example 8

Search for Candidate Transcription Factor Binding Sites

The 5'-flanking region of Siah-1 gene (nucleotide sequence shown in sequence table) was searched with a computer by TFSEARCH for potential binding to known transcription factors. The transcription factors used in the search were GATA-1, C/EBP, SRY, cdxA, CREB, GATA2, GATA3, NFκB, Sp1, N-myc, v-Myb and E2F.

As a result, several nucleotide sequences were identified which may bind to known transcription factors. These are the nucleotide sequences shown in base numbers 95-104, 158-170, 272-278, 320-326, 362-368, 438-444, 568-575, 753-762, 1383-1391, 1438-1447, 1509-1515, 1613-1619, 1649-1660, 1715-1724, 1728-1737, 1789-1797, 1826-1832, 1889-1895, 2058-2069, 2074-2078, 2103-2107, 2209-2216, 2219-2224, 2302-2307 and 2317-2324 of SEQ ID NO:2.

These are regions which activate or inhibit Siah-1 transcription by binding of specific substances Example 9

Confirming Promoter Activity and Determining Which Regions Contribute Chiefly to Promoter Activity Example 9-1

A 2515 by KpnI-NcoI fragment (base numbers 1-2515 in SEQ ID NO:2) containing the human Siah-1 promoter region obtained in Example 6 was subcloned into the KpnI-NcoI site of luciferase reporter plasmid pGVB2 (Japan, Tokyo, Nippon Gene). This plasmid was termed delKpnI.

A series of 5'-deletion mutants of the promoter region of this invention was generated from delKpnI using a "Kilo-sequence Deletion Kit" (Japan, Tokyo, Takara). These mutants are delPstI comprising base numbers 643-2515, delSmaI comprising base numbers 1290-2515, delBalI comprising base numbers 1410-2515, delMluI comprising base numbers 1683-2515, delNheI comprising base numbers 2035-2515 and delXhoI comprising base numbers 2383-2515 in the sequence table.

These plasmids were transiently transfected into MCF-7 cells

Specifically, MCF-7 cells ($1\times10^5$) were seeded in diam. 3.5 cm tissue culture plates, and after a 1 day culture, 2 µg of the aforementioned plasmid was transfected into the cells by the DEAE-dextran method (CellPhect Transfection Kit, Amersham Pharmacia, Code No. 27-9268-01). After 48 hours, luciferase activity in cell lysate was measured according to the protocols of a Pica Gene luminescence kit (Toyo Ink, Tokyo, Japan, Code No. 309-04321), and standardized by protein concentration in the cell lysate. Each experiment was repeated three times, and each luciferase assay was triplicated. Significance was tested using a Student's t-test, and differences were considered significant when p<0.05.

The results are shown in FIG. 3. As shown in FIG. 3, cells transfected with plasmid delKpnI having the full-length Siah-1 promoter (base numbers 1-2517 in SEQ ID NO:2) demonstrated extremely strong luciferase activity, confirming that the DNA shown in SEQ ID NO:2 in the sequence table is the Siah-1 gene promoter region.

No significant differences in luciferase activity were found among delKpnI having the full-length Siah-1 promoter, delPstI, delSmaI, delBalI, delMluI and delNheI, but there was a significant difference between delNheI and delXhoI. The luciferase activity of cells having delXhoI was virtually the same as that of cells having pGVB2, which has no inserted promoter region.

From this, it appears that transcription factors binding sites or enhancer sites essential for promoter activity of Siah-1 gene are present between bases number 2035-2382 of SEQ ID NO:2.

Example 9-2

Next, site-specific mutations were introduced into the two Sp1 sites (regions of base numbers 2221-2224 (CCCGCC) and 2302-2307 (GGCGGG) of Seq. No. 2) which are located in the region of base numbers 2035-2384, being shown in Example 9-2 to contribute to promoter activity, and which were shown in Example 8 to be candidate transcription factor binding sites.

Specifically, plasmid mSp1 having an introduced substitution mutation in the region of base numbers 2219-2224, plasmid mSp2 having an introduced substitution mutation in the region of base numbers 2302-2307, and plasmid mSp12 having introduced substitution mutations in both regions were prepared from luciferase reporter plasmid delNheI having inserted base numbers 2035-2515 of SEQ ID NO: 2, using a QuickChange Site-Directed Mutagenesis Kit (Stratagene) in accordance with the attached manual. In addition, 5'-deletion mutants del-Sp1 (having base numbers 2269-2515 and lacking the 5'-Sp1 site) and del-Sp12 (having base numbers 2311-2515 and lacking both Sp1 sites) of luciferase reporter plasmid delNheI were prepared using a "Kilo Sequence Deletion Kit" (Takara).

The mutated reporter plasmids were transiently transfected into MCF-7 cells, and luciferase activity of the cell lysate was measured, as shown in Example 9-1.

The nucleotide sequences and luciferase activities of the mutants are shown in FIG. 4. From FIG. 4, it is clear that luciferase activity declines significantly as a result of substitutions or deletions in the region of base numbers 2219-2224 in the nucleotide sequence of SEQ ID NO:2. From this, it appears that the region of base numbers 2219-2224 of the Siah-1 promoter regions contributes to basal promoter activity.

Example 10

Control of Siah-1 Gene by p53 Protein

Induction of endogenous Siah-1 expression by p53 protein was investigated as follows.

Human osteosarcoma Saos-2 cells ($1\times10^6$) with a complete deletion of p53 (null) mutation were seeded into Dulbecco's modified Eagle medium (DMEM, Nissui No. 05919) with 10% fetal calf serum, and incubated at 37° C. for 24 hours. Next, 10 µg of p53 expression plasmid p53pCMV-neoBam having p53 cDNA inserted into plasmid vector pCMV-neoBam (provided by Dr. B. Vogelstein) was transfected into Saos-2 cells using LIPOFECTAMINE PLUS (GIBCO) (containing 15 µl lipofectamine reagent, 10 µl PLUS reagent).

Saos-2 cells were sampled 12, 24 and 32 hours after transfection, and total RNA extracted with Sepasol (nacalai tesque) reagent. Ten µg of each of extracted total RNAs was subjected to agarose gel electrophoresis, transferred to a filter, and hybridized with Siah-1 cDNA labeled with an isotope.

Similar experiments were performed using erythroleukemic cell line K562 having a p53 mutation and human kidney epithelial cell line 293 having inactivated p53.

The results show that Siah-1 mRNA increased over time following transfection of p53 cDNA. This shows that Siah-1 expression is induced by p53 protein.

Example 11

Control of Siah-1 Gene by p53 protein

Human osteosarcoma Saos-2 cells ($1\times10^5$) with a complete deletion of p53 were seeded into Dulbecco's modified Eagle medium (DMEM, Nissui No. 05919) with 10% fetal calf serum, and incubated at 37° C. for 24 hours. Next, 20, 25 and 250 ng of p53 expression plasmid p53pCMV-neoBam (pCMV-neoBam plasmid was obtained from Dr. Vogelstein) having inserted p53 cDNA and 0.5 µg of luciferase reporter plasmid pGVB2 having inserted Siah-1 promoter region (comprising base numbers 1-2515 as well as approximately 1 kb upstream of SEQ ID NO:2 and including two p53 binding sequences) were transfected into Saos2 cells using LIPOFECTAMINE PLUS (GIBCO) (containing 1.5 µl lipofectamine reagent, 2.25 µl PLUS reagent).

Twenty-four hours after transfection, the Saos2 cells were sampled and luciferase activity of cell lysate was measured as shown in Example 6. In the results, p53 did not generate a significant increase in luciferase activity. This suggests that p53 may induce expression of Siah-1 through a site different from the p53 binding site of the Siah-1 promoter regions of the present invention.

From this, it appears that substances which induce Siah-1 expression by acting on the Siah-1 promoter region may be effective in normalizing process of p53 pathways in the case that p53 protein is inactivated by cancer, etc.

INDUSTRIAL APPLICABILITY

DR5 gene and Siah-1 gene are genes whose transcription is induced by p53 protein and which participate in suppression of cancer by causing apoptosis and cell cycle arrest. Consequently, the DR5 gene promoter and Siah-1 gene promoter of the present invention can be used favorably to screen substances which activate DR5 or Siah-1 gene at the transcription level by acting directly or indirectly thereon. Substances selected by the screening methods of the present invention are extremely effective for treatment of cancer and the like.

SEQUENCE LISTING

<160> NUMBER OF SEQ ID NOS: 12

Figure 1:
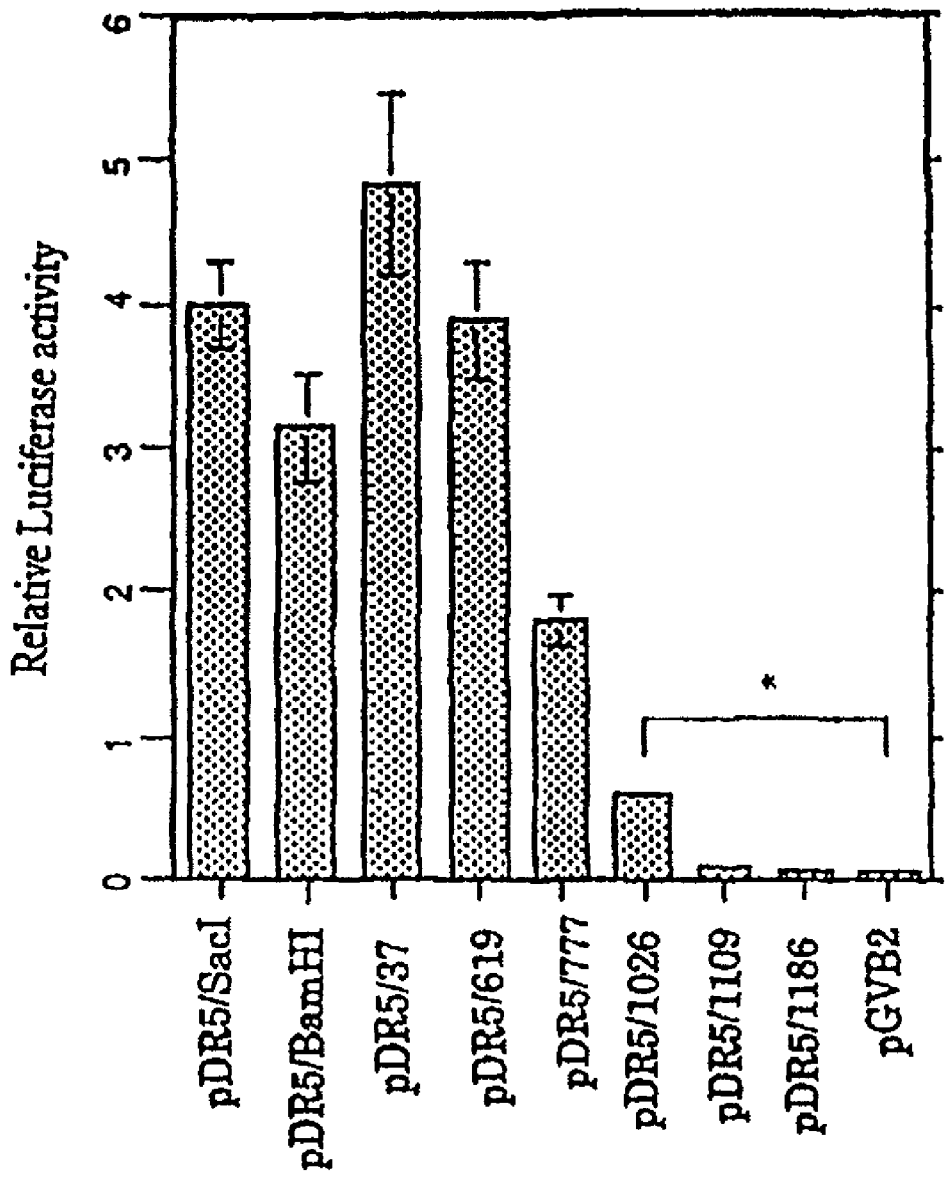
FIG. 1 shows changes in expressed amount of luciferase due to deletion mutations in the DR5 promoter region.
Figure 2:
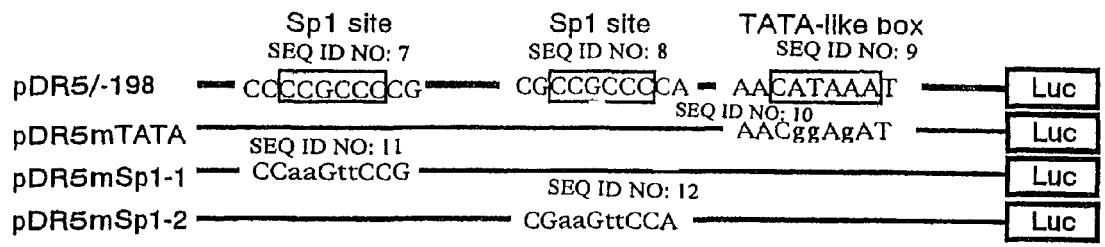
FIG. 2 shows changes in expressed amount of luciferase due to mutations in Sp1 sites of the DR5 promoter. (A) shows the nucleotide sequences of the mutants, while (B) is a graph showing expressed amount of luciferase.
Figure 2:
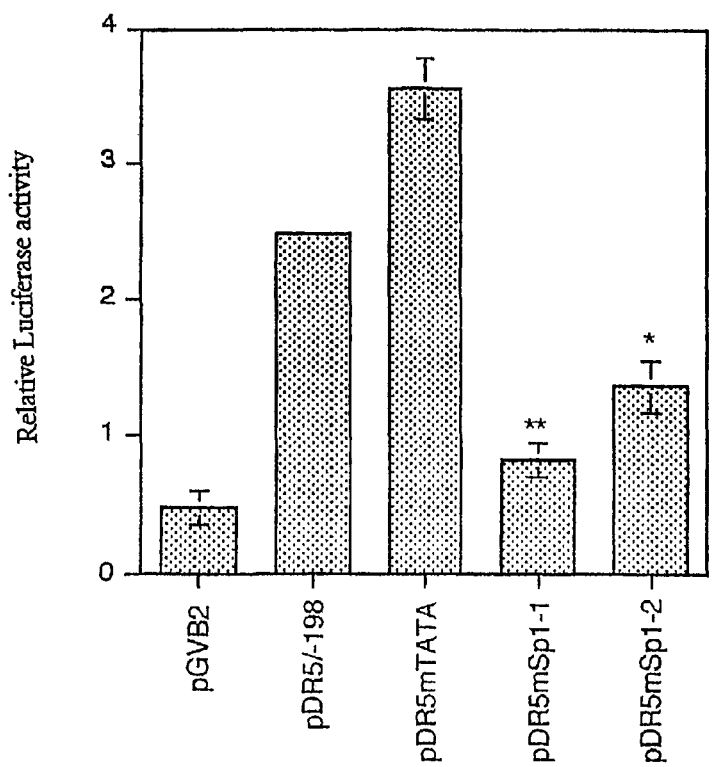
Figure 3:
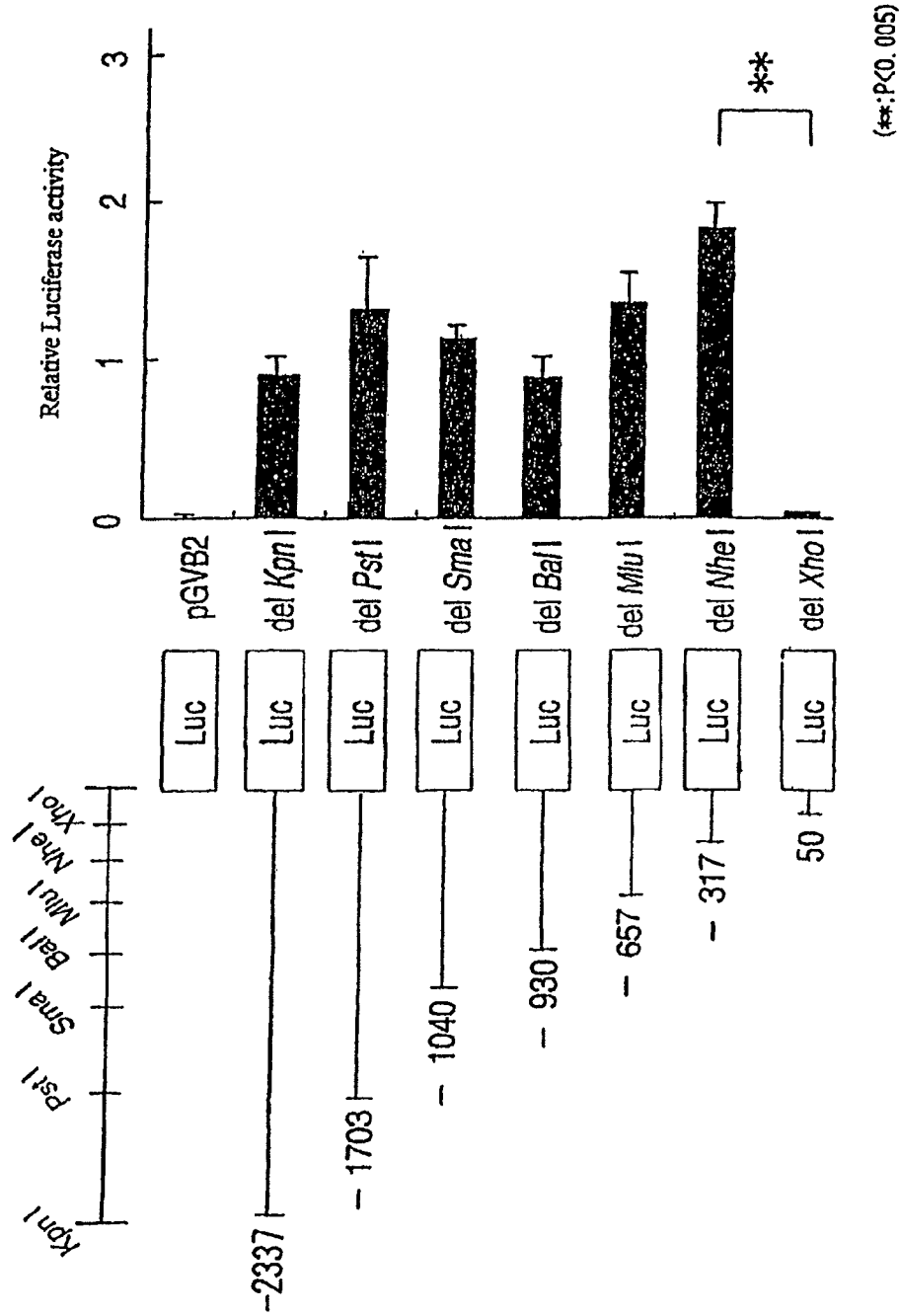
FIG. 3 shows changes in expressed amount of luciferase due to deletion mutations in the Siah-1 promoter region.
Figure 4:
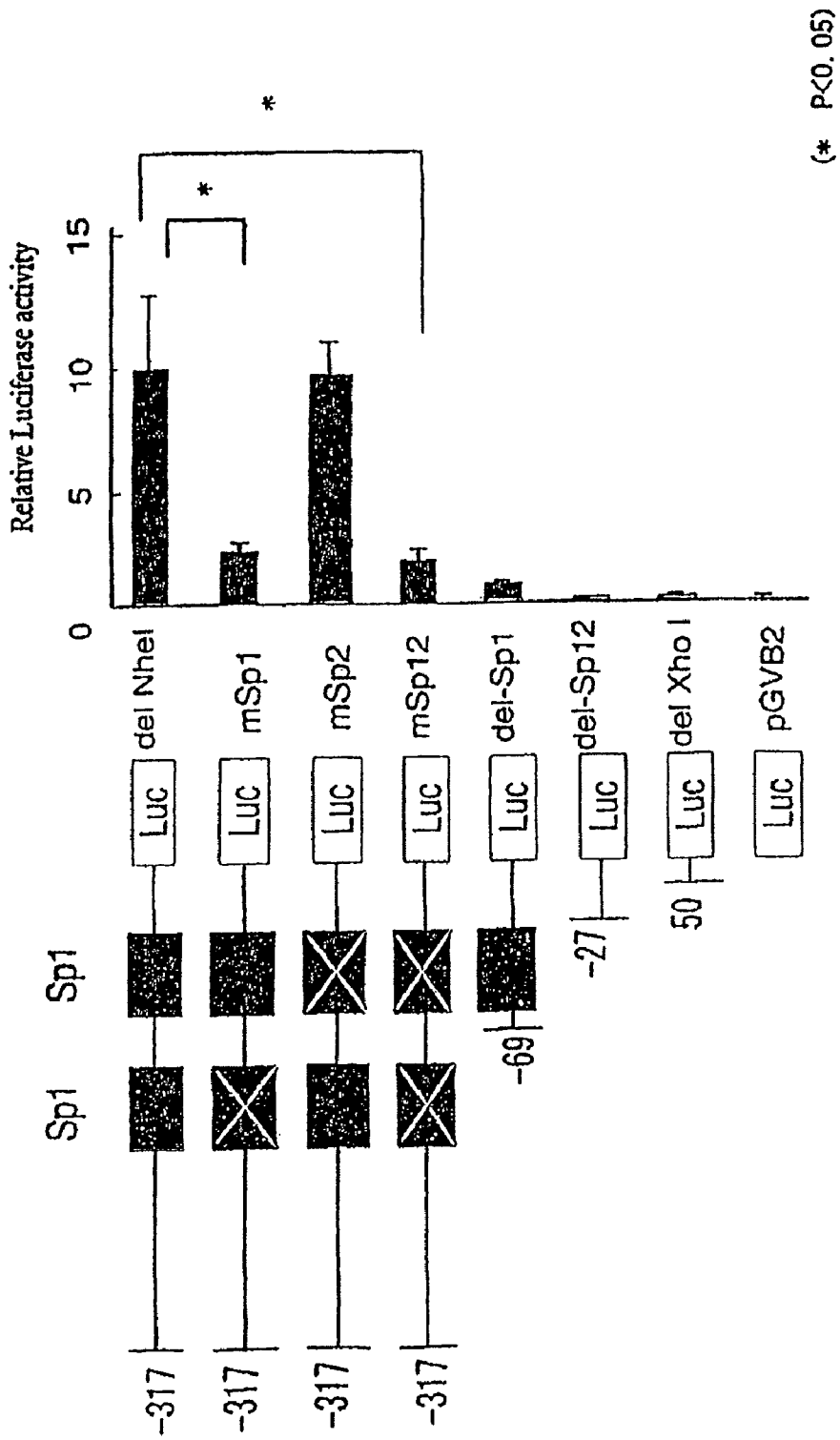
FIG. 4 shows changes in the expressed amount of luciferase due to mutations in Sp1 sites of the Siah-1 promoter.

<210> SEQ ID NO 1
<211> LENGTH: 1654

```
<212> TYPE: DNA
<213> ORGANISM: human

<400> SEQUENCE: 1
ctgcagcttc actcctgagc cagtgagacc acgaacccac cagaaggaag aaactccgaa      60
cacatccgaa catcagaagg aacaaactcc agacacgccg cctttaagaa ctgtaacact     120
caccgcgagg gtccgaggct tcattcttga aggcagtgag accaagaacc caccaattcc     180
ggacacagta ccatgaagga atgaaaatac ataacaatgt gatgtatcat gttttatttc     240
ctagactagt gacaaatgaa agctaagtgt agcaagggtg cagggacaca ggcacatttg     300
tggactaggt gtgagtgtaa gctgggttcg atggtctttt ggccaacata gtgaacccct     360
gtgtctacta aaatacaaa aattagccag gcgtggtggt gcaggcctgt agtcccagct     420
acatggaggc tgaggtggga gtatcgcttg aacctgggag acggaagttg cagtgagccg     480
ggatcacacc accgttcacc aatctgagcc acagagagac tgtctcaaaa aataaaccac     540
aaggaaggga gggaggggga gggggaggga gggaggaaag agaaagagag aaaggaagga     600 aagaaaagc aggaaggaag gaaagaagaa gaaagaagac gaaagaacga agaaaagga      660 aagaagagag gagagaacag aaggggcagg tgccccctggg aaggggagaa gatcaagacg     720
cgcctggaaa gcggactctg aacctcaaga ccctgttcac agccaagcgc gcgaccccgg     780
gaggcgtcaa ctccccaagt gcctccctca actcatttcc cccaagtttc ggtgcctgtc     840
ctggcgcgga caggacccag aaacaaacca cagcccgggg cgcagccgcc agggcgaagg     900
ttagttccgg tcccttcccc tccctcccc acttggacgc gcttgcggag gattgcgttg      960
acgagactct tatttattgt caccaacctg tggtggaatt tgcagttgca cattggatct    1020
gattcgcccc gccccgaatg acgcctgccc ggaggcagtg aaagtacagc cgcgccgccc    1080
caagtcagcc tggacacata aatcagcacg cggccggaga accccgcaat ctttgcgccc    1140
acaaaataca ccgacgatgc ccgatctact ttaagggctg aaaccacgg gcctgagaga     1200 ctataagagc gttccctacc gccatggaac aacggggaca gaacgccccg gccgcttcgg    1260
gggcccggaa aaggcacggc ccaggaccca ggggaggcgcg gggagccagg cctgggcccc    1320
gggtccccaa gacccttgtg ctcgttgtcg ccgcggtcct gctgttggtg agtccccgcc    1380
gcggtccctg gctggggaag agcgtgcctg gcgcctggag agggcagggt agagaggggg    1440
acacggcggg ggtgcgtggc ccgggtcgcc tgcggccggg catgtccggg caagacgcac    1500
cagtcgtcgg agtcggggga agagatgggt cccgggttg ggcaggagcg acctgggccg     1560
ccagggaaca gagcgcgcgc tccacttggt gtaaattccc gaatccagtg ggggagggcg    1620
acaaggaggg aattcccgag taagctgcgt gaag                                1654

<210> SEQ ID NO 2
<211> LENGTH: 2515
<212> TYPE: DNA
<213> ORGANISM: human

<400> SEQUENCE: 2
cttaactacg ggccagatgc aggaccagag cgttatgttc cattgcaata gatggaatta     60
ccatttgatg tgatttgagg ggaccaggaa ggctccctat ccagatgtgg cctgaaaata    120
tttgtcaccg ttactgaaat cccatcaatt ggaggattat ttggataggc tttacagttt    180
acaaaatgct tttctatgga taaactgtca aggaagcaga gtcaactccc tgttcagaaa    240
aggtgcttag ttaccccac agtggagcta ttttctttca aatggaaggt acattttttt     300
gagaggggga gtaaattaaa tttataatgg tgatgtttat gtcccaccca tagctaccac    360
```

```
ccagaattaa ccaaatcaga ttgagccccg cccaaatcta ggtaggaatt ctcagagatg      420
gaattaaccc gattaaattt gttttgtata aagggaagt ggggaaagta agaagtaact       480
tggactcttc tagaggagag caggcacaaa ctaagccaag aaaagcacgt ttgagaattc      540
cagaggcaga agttgcttct gggtgcctga cgtcaacgat ccagcacttc aagactggtg     600
tgcggcatcc tcaggggaca ctgtgtcctg ggcacccctg cagtttaaga gaatccacta    660
gtttataagg taagtcctcg actgtcagca gtgggccaga gacagactgt tatttcaga    720 tggacaaatg ctgttgggta gaggaaggga tgcgggataa ggaggacaaa atctgacttt    780
ggcaaagccg ggtgtttaga actttaatcg ccacgttggc aagttctctc ttagtccgta    840
tccatttcac tgcttgcaga gcggcccagg ggttctgggg gcgagaaaca catctcaccc    900
cagagctgct cctcgcccag acagaactc ctctgcccct cacgaccagg tcaaggccac     960
atggctatgc caagcacata gtctgtaaaa atggaaaatt tacctctaaa ctgaagtgaa    1020
ccgaactcta ttgaccttcc cgtgtactga ggagctataa cttctcccca aaatgtgaa     1080 agtaaaattg cagtttaaat catgtaatta ggaatactgt aaactagtgt tttgcacata    1140
taaactttat catacactgg gaatttgtac atacgtgccc ggtatgggat ttttctattt   1200
ttatttttat tttttgaga cagagtctcg ctctgttgtc caggctggag tgcaatggcc    1260
tgatctctgc ctcactgcaa cctctgcctc ccggttcaa gcgattctcc tgcctcagcc    1320
tccgagtagc tgggactaca ggcgtgcacc accacgcccg gctaatttt gtattttag     1380 tagagatagg gtttcaccat gttggccagg ctactctcga actcctgacc tcaggtaatc    1440
catcggcctc ggcctcccta agtgctggga ttacaggcgt gagccaccgc gtccggacgg    1500
aataccattt taatagatct tacatggaat tccagttagg gcttgtaaat gtctcagatg    1560
cttgcttctg ctcatagcac ccatcaaaga attgcaagtg atgttttcct tttattattt    1620
caagaagtgg aatgcagagt ccctaattag ggactttcca gatgagcatg gacacaggaa    1680
aacgcgtgct tccccattac ccacttttca gctgaaacaa gcttttgaag ctcgtcccgc    1740
tgttgctgag gagcggctca acctcggag aggctgggac tctctttagg ggtgggtcc     1800 cggtcggcgg gcagggcagc cgcttttct ttgggactga gtggagttgg gaaggatccg    1860
tggaggcgct gggctaaatc agcagacaaa acaaggggga gggcacaagg ccgcggcggc    1920
gggccagcct ggggctcgca tcccgctggg cgacccctcc ggccggagcc ggggggtca    1980 cgcggccccg gaacaaagcg ccgcgggagg agctgcctga ccgacgggc aagcgctagc    2040 ttctcgcggg ccagaggcgc cacgtgccag gatccgttga atgcgcggtg cacggcgca   2100 gcaacggtag ccgagtagcc cccgcaccta ctgccgcctt tggagacccg cacagctacg    2160
cccgcggagg ccgccgccgg ccgcgccaac gcctgtgcgc ctgcgcgccc gcgaaagccc   2220 cgcccccca ggctcccagc gcgcggggcc gcgcctcctc atggccgccg ccgcagtgtg    2280
tggtatttag cggggggcgcg cggcgggctc gaggacgcgc gaaacggcgg cggcggcggc   2340
caggggggag ccggggcggc cgttgcgggg cgcgctctcg agaggcgcg gcggcccagg    2400 gtgtcccgtc ggtctcggcg ccgggaagag gcggtggcgc tgcccgcggt ggcggggtt    2460 ggcgacggag cgcgttggtg ccaggaccgg ggtccgaggc gcgctctccg cccac         2515
```

<210> SEQ ID NO 3
<211> LENGTH: 30
<212> TYPE: DNA
<213> ORGANISM: human

<400> SEQUENCE: 3

-continued ccgcaatctc tgcgcccaca aaatacaccg                              30

<210> SEQ ID NO 4
<211> LENGTH: 30
<212> TYPE: DNA
<213> ORGANISM: human

<400> SEQUENCE: 4
gtttcagccc ttaaagtaga tcgggcatcg                              30

<210> SEQ ID NO 5
<211> LENGTH: 30
<212> TYPE: DNA
<213> ORGANISM: human

<400> SEQUENCE: 5
gacggagcgc gttggtgcca ggaccggggt                              30

<210> SEQ ID NO 6
<211> LENGTH: 30
<212> TYPE: DNA
<213> ORGANISM: human

<400> SEQUENCE: 6
ttcccggcgc cgagaccgac gggacaccct                              30

<210> SEQ ID NO 7
<211> LENGTH: 10
<212> TYPE: DNA
<213> ORGANISM: human

<400> SEQUENCE: 7
ccccgccccg                                                    10

<210> SEQ ID NO 8
<211> LENGTH: 10
<212> TYPE: DNA
<213> ORGANISM: human

<400> SEQUENCE: 8
cgccgcccca                                                    10

<210> SEQ ID NO 9
<211> LENGTH: 9
<212> TYPE: DNA
<213> ORGANISM: human

<400> SEQUENCE: 9 aacataaat                                                      9

<210> SEQ ID NO 10
<211> LENGTH: 9
<212> TYPE: DNA
<213> ORGANISM: human

<400> SEQUENCE: 10 aacggagat                                                      9

<210> SEQ ID NO 11
<211> LENGTH: 10
<212> TYPE: DNA
<213> ORGANISM: human

<400> SEQUENCE: 11

```
ccaagttccg                                                              10

<210> SEQ ID NO 12
<211> LENGTH: 10
<212> TYPE: DNA
<213> ORGANISM: human

<400> SEQUENCE: 12
cgaagttcca                                                              10
```

The invention claimed is:

1. A DNA consisting of a successive nucleotide sequence selected from the nucleotide sequence of base numbers 1-1477 of SEQ ID NO:1, wherein the successive nucleotide sequence comprises at least the nucleotide sequence of base numbers 1026-1108 of SEQ ID NO:1, and wherein said DNA functions as a promoter.

2. A DNA according to claim 1, wherein the successive nucleotide sequence consists of the nucleotide sequence of base numbers 1-1223 of SEQ ID No:1.

3. The DNA according to claim 1, wherein the successive nucleotide sequence consists of the nucleotide sequence of base numbers 1-1108 of SEQ ID No:1.

4. The DNA according to claim 1, wherein the successive nucleotide sequence consists of the nucleotide sequence of base numbers 619-1223 of SEQ ID No:1.

5. The DNA according to claim 1, wherein the successive nucleotide sequence consists of the nucleotide sequence of base numbers 777-1223 of SEQ ID No:1.

6. The DNA according to claim 1, wherein the successive nucleotide sequence consists of the nucleotide sequence of base numbers 1026-1223 of SEQ ID No:1.

7. A vector comprising the DNA according to claim 1.
8. A vector comprising the DNA according to claim 2.
9. A vector comprising the DNA according to claim 3.
10. A vector comprising the DNA according to claim 4.
11. A vector comprising the DNA according to claim 5.
12. A vector comprising the DNA according to claim 6.
13. Cells containing the vector of claim 7.
14. Cells containing the vector of claim 8.
15. Cells containing the vector of claim 9.
16. Cells containing the vector of claim 10.
17. Cells containing the vector of claim 11.
18. Cells containing the vector of claim 12.

* * * * *